United States Patent
Keal et al.

(10) Patent No.: US 10,534,014 B2
(45) Date of Patent: Jan. 14, 2020

(54) SYSTEM AND METHOD FOR DROP DETECTION

(71) Applicant: InvenSense, Inc., San Jose, CA (US)

(72) Inventors: William Kerry Keal, Santa Clara, CA (US); James Lim, Saratoga, CA (US)

(73) Assignee: InvenSense, Inc., San Jose, CA (US)

( * ) Notice: Subject to any disclaimer, the term of this patent is extended or adjusted under 35 U.S.C. 154(b) by 1265 days.

(21) Appl. No.: 14/464,817

(22) Filed: Aug. 21, 2014

(65) Prior Publication Data

US 2016/0054354 A1    Feb. 25, 2016

(51) Int. Cl.
| | |
|---|---|
| *G01P 15/18* | (2013.01) |
| *G01C 19/5776* | (2012.01) |
| *G01P 15/16* | (2013.01) |
| *A61B 5/11* | (2006.01) |
| *G01C 25/00* | (2006.01) |
| *A61B 5/00* | (2006.01) |

(52) U.S. Cl.
CPC .......... *G01P 15/18* (2013.01); *G01C 19/5776* (2013.01); *G01P 15/16* (2013.01)

(58) Field of Classification Search
CPC ...... G01P 15/0891; G01P 15/18; G01P 15/16; A61B 5/0024; A61B 5/11; A61B 5/721; G06Q 10/087; G06T 5/002; H04M 1/72522; G01C 19/5776; G01C 25/005
USPC ............ 702/141; 700/595; 706/52; 358/3.26
See application file for complete search history.

(56) References Cited

U.S. PATENT DOCUMENTS

| | | | |
|---|---|---|---|
| 5,323,337 A | 6/1994 | Wilson et al. | |
| 6,758,080 B1 | 7/2004 | Ragan et al. | |
| 7,599,575 B2 * | 10/2009 | Lienard | ............ G06T 5/002 |
| | | | 358/3.26 |
| 2003/0036847 A1 | 2/2003 | Geier et al. | |
| 2004/0168797 A1 | 9/2004 | Barrow | |
| 2005/0251328 A1 | 11/2005 | Merwe et al. | |
| 2005/0283988 A1 | 12/2005 | Sato et al. | |
| 2006/0116848 A1 * | 6/2006 | Clifford | ............ G01P 15/0891 |
| | | | 702/141 |
| 2006/0229869 A1 | 10/2006 | Nemer | |
| 2006/0282021 A1 * | 12/2006 | DeVaul | ............ A61B 5/0024 |
| | | | 600/595 |
| 2008/0262728 A1 | 10/2008 | Lokshin et al. | |
| 2009/0007661 A1 | 1/2009 | Nasiri et al. | |

(Continued)

FOREIGN PATENT DOCUMENTS

WO    2000055652 A1    9/2000

OTHER PUBLICATIONS

International Preliminary Report dated Mar. 2, 2017 for PCT Patent Application No. PCT/US15/41060.

(Continued)

*Primary Examiner* — Regis J Betsch
*Assistant Examiner* — Kaleria Knox
(74) *Attorney, Agent, or Firm* — Bay Area Technology Law Group PC (57) ABSTRACT

A system and method for reliably detecting when a device has been dropped. In a non-limiting example, a drop detection system may be operable to perform one or more of: fall detection, end-of-fall detection, and/or detection of no motion after the fall. The drop detection system may, for example, analyze information from one or more MEMS sensors on-board the device to detect when the device has been dropped.

29 Claims, 5 Drawing Sheets

(56) References Cited

U.S. PATENT DOCUMENTS

2010/0250481 A1* 9/2010 Tomastik .............. G06Q 10/087
　　　　　　　　　　　　　　　　　　　　　706/52
2010/0292943 A1　11/2010　Minor et al.
2012/0323520 A1　12/2012　Keal
2015/0317893 A1* 11/2015　Tseng ................ H04M 1/72522
　　　　　　　　　　　　　　　　　　　　　340/686.1

OTHER PUBLICATIONS

International Search Report and Written Opinion dated Aug. 16, 2012 for International Application No. PCT/US12135848, 10 pages.
Delaney, "Signal Detection Using Third-Order Moments", 1994, Circuits, Systems and Signal Processing vol. 13, Issue 4, pp. 481-496.
International Search Report and Written Opinion corresponding to International Patent Application No. PCT/US15/41060 dated Oct. 23, 2015.

* cited by examiner

SYSTEM AND METHOD FOR DROP DETECTION

CROSS-REFERENCE TO RELATED APPLICATIONS/INCORPORATION BY REFERENCE

This patent application is related to patent application Ser. No. 13/164,136 filed Jun. 20, 2011, and titled "MOTION DETERMINATION," the contents of which are hereby incorporated herein by reference in their entirety.

FEDERALLY SPONSORED RESEARCH OR DEVELOPMENT

[Not Applicable]

SEQUENCE LISTING

[Not Applicable]

MICROFICHE/COPYRIGHT REFERENCE

[Not Applicable]

BACKGROUND

Consumer devices generally do not perform drop detection in an efficient and reliable manner. For example, hand-held and/or wearable consumer devices generally do not efficiently and reliably determine when the device has been dropped. Further limitations and disadvantages of conventional and traditional approaches will become apparent to one of skill in the art, through comparison of such approaches with the disclosure as set forth in the remainder of this application with reference to the drawings.

SUMMARY

Various aspects of this disclosure provide a system and method for reliably detecting when a device has been dropped, substantially as shown in and/or described in connection with at least one of the figures, as set forth more completely in the claims. In a non-limiting example, a drop detection system may be operable to perform one or more of: fall detection, end-of-fall detection, and/or detection of no motion after the fall. The drop detection system may, for example, analyze information from one or more MEMS sensors on-board the device to detect when the device has been dropped

DETAILED DESCRIPTION OF VARIOUS ASPECTS OF THE DISCLOSURE

The following discussion presents various aspects of the present disclosure by providing various examples thereof. Such examples are non-limiting, and thus the scope of various aspects of the present disclosure should not necessarily be limited by any particular characteristics of the provided examples. In the following discussion, the phrases "for example" and "e.g." and "exemplary" are non-limiting and are generally synonymous with "by way of example and not limitation," "for example and not limitation," and the like.

The following discussion may at times utilize the phrase "A and/or B." Such phrase should be understood to mean A, or B, or both A and B. Similarly, the phrase "A, B, and/or C" should be understood to mean A, B, C, A and B, A and C, B and C, or all of A and B and C.

The following discussion may at times utilize the phrases "operable to," "operates to," and the like in discussing functionality performed by particular hardware, including hardware operating in accordance with software instructions. The phrases "operates to," "is operable to," and the like include "operates when enabled to." For example, a module that operates to perform a particular operation, but only after receiving a signal to enable such operation, is included by the phrases "operates to," "is operable to," and the like.

The following discussion may at times refer to various system or device functional modules. It should be understood that the functional modules were selected for illustrative clarity and not necessarily for providing distinctly separate hardware and/or software modules. For example, any one or more of the modules discussed herein may be implemented by shared hardware, including for example a shared processor. Also for example, any one or more of the modules discussed herein may share software portions, including for example subroutines. Additionally for example, any one or more of the modules discussed herein may be implemented with independent dedicated hardware and/or software. Accordingly, the scope of various aspects of this disclosure should not be limited by arbitrary boundaries between modules unless explicitly claimed.

In various example embodiments discussed herein, a chip is defined to include at least one substrate typically formed from a semiconductor material. A single chip may for example be formed from multiple substrates, where the substrates are mechanically bonded and electrically connected to preserve the functionality. Multiple chip (or multi-chip) includes at least 2 substrates, wherein the 2 substrates are electrically connected, but do not require mechanical bonding.

A package provides electrical connection between the bond pads on the chip (or for example a multi-chip module) to a metal lead that can be soldered to a printed circuit board (or PCB). A package typically comprises a substrate and a cover. An Integrated Circuit (IC) substrate may refer to a silicon substrate with electrical circuits, typically CMOS circuits. A MEMS substrate provides mechanical support for the MEMS structure(s). The MEMS structural layer is attached to the MEMS substrate. The MEMS substrate is also referred to as handle substrate or handle wafer. In some embodiments, the handle substrate serves as a cap to the MEMS structure.

In the described embodiments, an electronic device incorporating a sensor may, for example, employ a motion tracking module also referred to as Motion Processing Unit (MPU) that includes at least one sensor in addition to electronic circuits. The at least one sensor may comprise any of a variety of sensors, such as for example a gyroscope, a compass, a magnetometer, an accelerometer, a microphone, a pressure sensor, a proximity sensor, a moisture sensor, a temperature sensor, a biometric sensor, or an ambient light sensor, among others known in the art.

Some embodiments may, for example, comprise an accelerometer, gyroscope, and magnetometer or other compass technology, which each provide a measurement along three axes that are orthogonal relative to each other, and may be referred to as a 9-axis device. Other embodiments may, for example, comprise an accelerometer, gyroscope, compass, and pressure sensor, and may be referred to as a 10-axis device. Other embodiments may not include all the sensors or may provide measurements along one or more axes.

The sensors may, for example, be formed on a first substrate. Various embodiments may, for example, include solid-state sensors and/or any other type of sensors. The electronic circuits in the MPU may, for example, receive measurement outputs from the one or more sensors. In various embodiments, the electronic circuits process the sensor data. The electronic circuits may, for example, be implemented on a second silicon substrate. In some embodiments, the first substrate may be vertically stacked, attached and electrically connected to the second substrate in a single semiconductor chip, while in other embodiments, the first substrate may be disposed laterally and electrically connected to the second substrate in a single semiconductor package.

In an example embodiment, the first substrate is attached to the second substrate through wafer bonding, as described in commonly owned U.S. Pat. No. 7,104,129, which is hereby incorporated herein by reference in its entirety, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

In the described embodiments, raw data refers to measurement outputs from the sensors which are not yet processed. Motion data refers to processed raw data. Processing may, for example, comprise applying a sensor fusion algorithm or applying any other algorithm. In the case of a sensor fusion algorithm, data from one or more sensors may be combined and/or processed to provide an orientation of the device. In the described embodiments, a MPU may include processors, memory, control logic and sensors among structures.

Drop detection, for example for an electronic device, is useful. For example, a device vendor may desire to determine whether a device brought in for warranty repair or replacement has been mishandled by the user. Conventional systems, for example mobile consumer devices, either do not perform drop detection or do not perform drop detection in an efficient and reliable manner. For example, conventional systems may identify a drop event when no drop has occurred and/or fail to identify a drop event when a drop has occurred. Further, all device drops are not equally significant. For example, a device being dropped on the floor is not the same as a device being tossed on a sofa or bed. Additionally for example, a device being tossed in the air and caught is not the same as a device falling to the ground.

Drop (or impact) detection and/or characterization may, for example, be useful during operation of the device. For example, a detected drop and/or a drop of a particular type may trigger various operations of the device to be performed. For example, a detected drop and/or impact may cause a device to turn off a screen. Also for example, a detected drop and/or drop of a particular type may cause a device to enter a low-power mode (e.g., turning off a display, turning off or reducing positioning functionality, turning off or reducing wireless LAN and/or personal LAN communication functionality, etc.). In an example scenario, when a user drops or tosses a mobile phone on a seat, sofa, or bed, the device may enter a low-power state.

Accordingly, various aspects of the present disclosure provide non-limiting examples of methods and systems for efficient and reliable drop detection. The discussion will now turn to discussing the attached figures.

Figure 1:
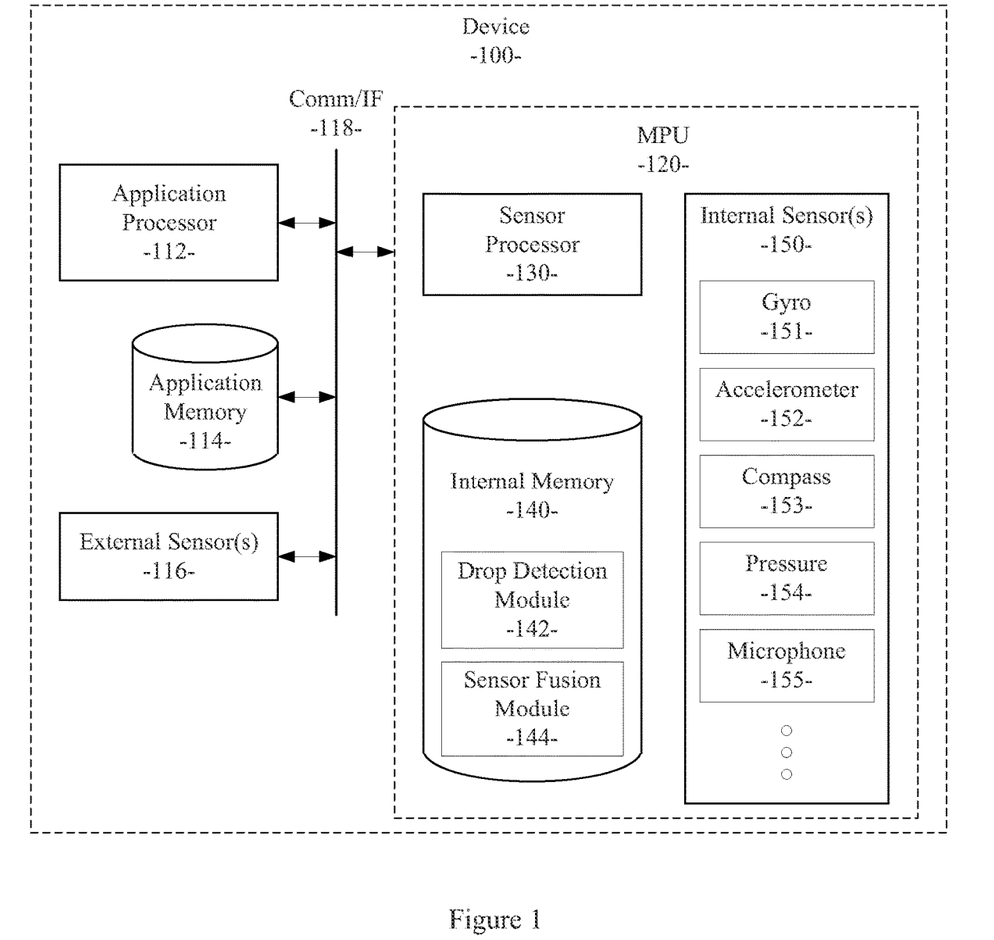
FIG. 1 shows a block diagram of an example electronic device comprising drop detection capability, in accordance with various aspects of the present disclosure.

Turning first to FIG. 1, such figure shows a block diagram of an example electronic device 100 comprising drop detection capability, in accordance with various aspects of the present disclosure. As will be appreciated, the device 100 may be implemented as a device or apparatus, such as a handheld and/or wearable device that can be moved in space by a user and its motion and/or orientation in space therefore sensed. For example, such a handheld device may be a mobile phone (e.g., a cellular phone, a phone running on a local network, or any other telephone handset), wired telephone (e.g., a phone attached by a wire and/or optical tether), personal digital assistant (PDA), personal activity and/or health monitoring device, video game player, video game controller, navigation device, mobile internet device (MID), personal navigation device (PND), digital still camera, digital video camera, binoculars, telephoto lens, portable music, video, or media player, remote control, or other handheld device, or a combination of one or more of these devices.

In some embodiments, the device 100 may be a self-contained device that comprises its own display and/or other output devices in addition to input devices as described below. However, in other embodiments, the device 100 may function in conjunction with another portable device or a non-portable device such as a desktop computer, electronic tabletop device, server computer, etc., which can communicate with the device 100, e.g., via network connections. The device may, for example, be capable of communicating via a wired connection using any type of wire-based communication protocol (e.g., serial transmissions, parallel transmissions, packet-based data communications), wireless connection (e.g., electromagnetic radiation, infrared radiation or other wireless technology), or a combination of one or more wired connections and one or more wireless connections.

As shown, the example device 100 comprises an MPU 120, application (or host) processor 112, application (or host) memory 114, and may comprise one or more sensors, such as external sensor(s) 116. The application processor 112 may, for example, be configured to perform the various computations and operations involved with the general function of the device 100. The application processor 112 may, for example, be coupled to MPU 120 through a communication interface 118, which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial peripheral interface (SPI) bus, a serial digital input output (SDIO) bus, or other equivalent. The application memory 114 may comprise programs, drivers or other data that utilize information provided by the MPU 120. Details regarding example suitable configurations of the application (or host) processor 112 and MPU 120 may be found in co-pending, commonly owned U.S. patent application Ser. No. 12/106,921, filed Apr. 21, 2008, which is hereby incorporated by reference in its entirety.

In this example embodiment, the MPU 120 is shown to comprise a sensor processor 130, internal memory 140 and one or more internal sensors 150. The internal sensors 150 comprise a gyroscope 151, an accelerometer 152, a compass 153 (for example a magnetometer), a pressure sensor 154, and a microphone 155. Though not shown, the internal sensors 150 may comprise any of a variety of sensors, for example, a proximity sensor, temperature sensor, light sensor, moisture sensor, biometric sensor, etc. The internal sensors 150 may, for example, be implemented as MEMS-based motion sensors, including inertial sensors such as a gyroscope or accelerometer, or an electromagnetic sensor such as a Hall effect or Lorentz field magnetometer. As desired, one or more of the internal sensors 150 may be configured to provide raw data output measured along three orthogonal axes or any equivalent structure. The internal memory 140 may store algorithms, routines or other instructions for processing data output by one or more of the internal sensors 120, including the drop detection module 142 and sensor fusion module 144, as described in more detail herein. If provided, external sensor(s) 116 may comprise one or more sensors, such as accelerometers, gyroscopes, magnetometers, pressure sensors, microphones, proximity sensors, and ambient light sensors, biometric sensors, temperature sensors, and moisture sensors, among other sensors. As used herein, an internal sensor generally refers to a sensor implemented, for example using MEMS techniques, for integration with the MPU 120 into a single chip. Similarly, an external sensor as used herein generally refers to a sensor carried on-board the device 100 that is not integrated into the MPU 120.

Even though various embodiments may be described herein in the context of internal sensors implemented in the MPU 120, these techniques may be applied to a non-integrated sensor, such as an external sensor 116, and likewise drop detection module 142 may be implemented using instructions stored in any available memory resource, such as for example the application memory 114, and may be executed using any available processor, such as for example the application processor 112. Still further, the functionality performed by the drop detection module may be implemented using any combination of hardware, firmware and software.

As will be appreciated, the application (or host) processor 112 and/or sensor processor 130 may be one or more microprocessors, central processing units (CPUs), microcontrollers or other processors, which run software programs for the device 100 and/or for other applications related to the functionality of the device 100. For example, different software application programs such as menu navigation software, games, camera function control, navigation software, and telephone, or a wide variety of other software and functional interfaces, can be provided. In some embodiments, multiple different applications can be provided on a single device 100, and in some of those embodiments, multiple applications can run simultaneously on the device 100. Multiple layers of software can, for example, be provided on a computer readable medium such as electronic memory or other storage medium such as hard disk, optical disk, flash drive, etc., for use with application processor 112 and sensor processor 130. For example, an operating system layer can be provided for the device 100 to control and manage system resources in real time, enable functions of application software and other layers, and interface application programs with other software and functions of the device 100. In various example embodiments, one or more motion algorithm layers may provide motion algorithms for lower-level processing of raw sensor data provided from internal or external sensors. Further, a sensor device driver layer may provide a software interface to the hardware sensors of the device 100. Some or all of these layers can be provided in the application memory 114 for access by the application processor 112, in internal memory 140 for access by the sensor processor 130, or in any other suitable architecture (e.g., including distributed architectures).

In some example embodiments, it will be recognized that the example architecture depicted in FIG. 1 may provide for drop detection to be performed using the MPU 120 and might not require involvement of the application processor 112 and/or application memory 114. Such example embodiments may, for example, be implemented with one or more internal sensor sensors 150 on a single substrate. Moreover, as will be described below, the drop detection techniques may be implemented using computationally efficient algorithms to reduce processing overhead and power consumption.

As discussed herein, various aspects of this disclosure may, for example, comprise processing various sensor signals indicative of device orientation. Non-limiting examples of such signals are signals that indicate acceleration along the z-axis (or gravitational axis) in a world coordinate system.

In an example implementation, an accelerometer and/or associated circuitry may output a vector indicative of device (or accelerometer) acceleration. For example, such a vector may express respective acceleration components along the x, y, and z axes of a body (or device, or component) coordinate system. Such a vector may be processed by a transformation function, for example based on sensor fusion calculations, that transforms the accelerometer vector to a world coordinate system (e.g., based on gyroscope signals, compass signals, etc.). For example, an accelerometer vector $[A_b^x, A_b^y, A_b^z]$ in body (or device or component) coordinates may be transformed to an accelerometer vector $[A_w^x, A_w^y, A_w^z]$ in world coordinates.

Portions of discussion herein may focus on the z-axis component of the accelerometer vector expressed in the world coordinate system, for example $A_w^z$. Other portions of the discussion herein may focus on the x, y, and/or z axes of the accelerometer vector expressed in the world coordinate system, for example $[A_w^x, A_w^y, A_w^z]$. Still other portions of the discussion herein may focus on the x, y, and/or z axes of the accelerometer vector expressed in the body coordinate system, for example $[A_b^x, A_b^y, A_b^z]$. Accordingly, the scope of this disclosure is not limited by the particular signal(s) and/or signal combinations discussed herein.

Device drop scenarios comprise various characteristics. The more of such characteristics that can be detected (or suspected), the more accurate a drop determination may become. For example, turning next to FIG. 2, such figure shows a timeline 200 illustrating an example sequence of events associated with a device drop scenario, in accordance with various aspects of the present disclosure.

Figure 2:
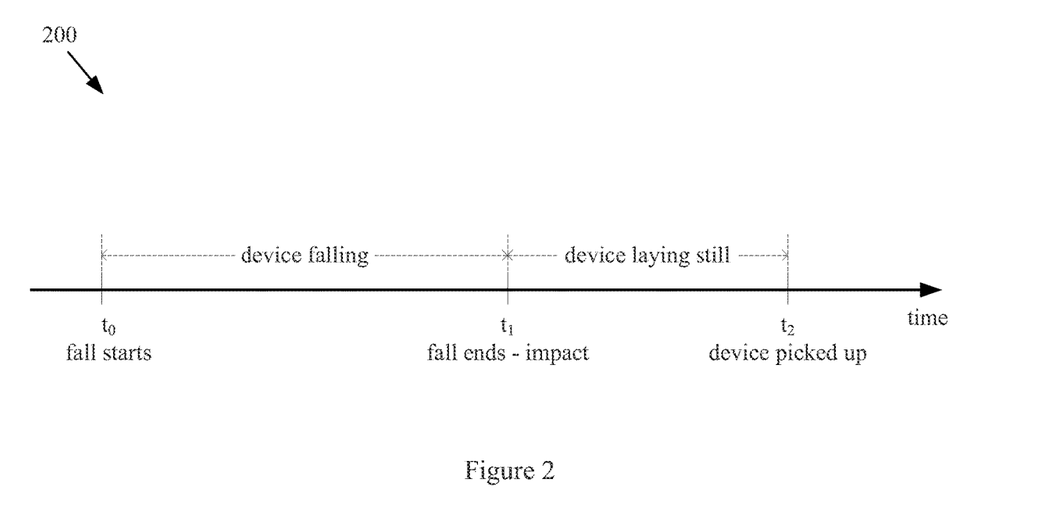
FIG. 2 shows a timeline illustrating an example sequence of events associated with a device drop scenario, in accordance with various aspects of the present disclosure.

At time $t_0$, a device (e.g., many examples of which are provided herein) begins falling. At time $t_1$, the fall ends with an impact (e.g., a device hitting a floor, a sidewalk, a road, a desk, etc.). At time $t_2$, the fallen device is picked up. Between time $t_0$ and time $t_1$, the device is in a free-falling state. Between time $t_1$ and time $t_2$, the device is laying still after the fall and impact (e.g., the device has not yet been picked up by the user).

The example device fall sequence illustrated in FIG. 2, and other similar sequences, may be detected in any of a variety of manners, non-limiting examples of which are presented herein. A number of such non-limiting examples will now be discussed with regard to FIGS. 3-5.

Figure 3:
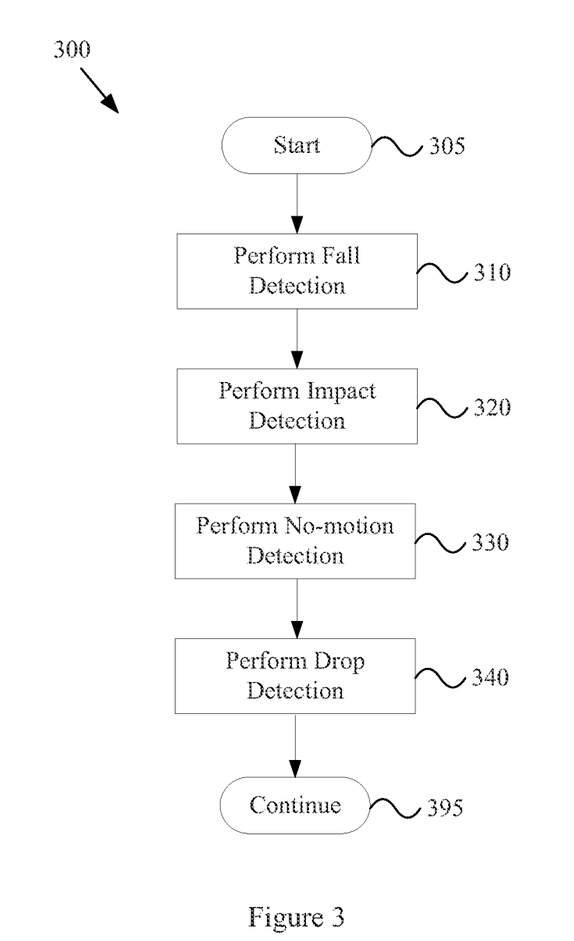
FIG. 3 shows a flow diagram illustrating an example method for determining whether a device has been dropped, in accordance with various aspects of the present disclosure.

Turning now to FIG. 3, such figure shows a flow diagram illustrating an example method 300 for determining whether a device has been dropped, in accordance with various aspects of the present disclosure. Any or all of the blocks of the example method 300 may, for example, be implemented by the MPU 120 of the device 100 shown in FIG. 1, for example executing software instructions stored in the drop detection software module 142. Additionally for example, any or all of the blocks of the example method 300 may be implemented by the application (or host) processor 112 of the device 100 shown in FIG. 1, for example executing software instructions stored in the external memory 116.

The example method 300 may begin executing at block 305. The method 300 may begin executing in response to any of a variety of causes or conditions. For example, the method 300 may continually (e.g., periodically) run. For example, the method 300 may begin executing at a constant period (e.g., every 10 ms, every 50 ms, every 100 ms, every 200 ms, etc.). Additionally for example, the method 300 may begin operating when sensor information being analyzed is updated (e.g., at a sensor update rate). Also for example, the method 300 may begin executing in response to a substantial noise (e.g., an audible exclamation that often accompanies a dropped device, the sound of a phone being removed from a pocket or purse, etc.). Further for example, the method 300 may begin executing in response to one or more sensors (or a sensor fusion output) indicating that the orientation and/or elevation of the device has substantially changed (e.g., based on a rotation that often accompanies a falling device). In general, the method 300 may begin executing in response to any of a variety of causes or conditions. Accordingly, the scope of various aspects of this disclosure should not be limited by characteristics of any particular one or more causes or conditions.

From block 305, execution flow of the example method 300 proceeds to block 310. Block 310 may, for example, comprise performing fall detection, for example determining whether a device is falling. Block 310 may comprise performing fall detection in any of a variety of manners, non-limiting examples of which are provided herein.

In a first example manner, for example in an implementation in which no motion (or stillness) results in a detected acceleration force corresponding to gravity and in which a fall results in no or little detected acceleration force, block 310 may comprise processing one or more accelerometer vector components expressed in the body coordinate system of the device, for example one or more of $[A_b^x, A_b^y, A_b^z]$. Similarly, a component coordinate system of the MPU may also be utilized. For example, block 310 may comprise determining whether the sum of one or more of the acceleration vector components squared is less than an acceleration fall threshold and/or less than an acceleration fall threshold for at least a minimum amount of time. For example:

$$\text{If } ([(A_b^x)^2 + (A_b^y)^2 + (A_b^z)^2] < \text{Th\_Accel}_{fall\ max} \text{ and } t_{fall} > \text{Th\_Time}_{fall\ min}) \qquad \text{Equation 1:}$$

The acceleration fall threshold (Th_Accel$_{fall\ max}$) may, for example, be a constant that is near zero, at 1 m/s$^2$, at 2 m/s$^2$, etc. For example, the acceleration fall threshold may be an expected value for free fall, plus a buffer amount (e.g., to allow for noise). The acceleration fall threshold (Th_Accel$_{fall\ max}$) and/or time fall threshold (Th_Time$_{fall\ min}$) may, for example, be programmable. For example, in a scenario in which the MPU 120 (which may, for example, comprise a chip and/or package separate from the application processor 112 or integrated therewith) is implementing block 310, the MPU 120 may comprise an interface (e.g., a register-based interface, a FIFO-based interface, etc.) by which the application processor 112 may program any or all of the threshold values discussed herein (e.g., upon system initialization, upon empirically determining adjustments, etc.). Note that block 310 may comprise averaging or otherwise filtering (e.g., IIR-filtering) the accelerometer vector coefficients, for example to reduce the impact of a single instantaneous signal (e.g., a noisy signal comprising environmental noise, device imperfections, etc.) on the calculation.

For the time threshold comparison, block 310 may, for example, comprise utilizing a counter and a counter threshold, for example, Cntr>Cntr$_{fall\ min}$, to implement the time threshold aspect of Equation 1 (e.g., $t_{fall}$>Th_Time$_{fall\ min}$). A minimum falling time threshold may, for example, assist in distinguishing between a free fall and a motion that occurs during normal non-falling device utilization, for example swinging in or attached to a hand, bouncing in a pocket, returning a device to a packet, shaking a device, attached to an ankle of other part of the leg, etc.

In another example, block 310 may comprise determining whether the sum of the magnitudes of one or more of the acceleration vector components is less than a threshold and/or less than a threshold for at least a minimum amount of time. For example:

$$\text{If } [|A_b^x| + |A_b^y| + |A_b^z|] < \text{Th\_Accel}_{fall\ max} \text{ and } t_{fall} > \text{Th\_Time}_{fall\ min}) \qquad \text{Equation 2:}$$

In another example system, rather than (or in addition to) analyzing acceleration vector components in a device body coordinate system, block 310 may comprise performing the analysis in a world (or inertial) coordinate system. As discussed above, an acceleration vector may be transformed to the world coordinate system, for example utilizing a sensor fusion module in a device that comprises a gyroscope and/or compass.

For example, in an example system, the z-axis in the world coordinate system may point up or down relative to the earth. For example, orientation information may be utilized to decouple device rotation motion and a falling motion. Also for example, acceleration forces or the lack thereof due to falling may be decoupled from acceleration forces, for example centrifugal forces, due to device rotation. In such a scenario, block 310 may comprise determining whether the square and/or amplitude of the z-axis component of the acceleration vector expressed in the world coordinate system, where the z-axis is aligned with gravity, is less than an acceleration fall threshold and/or less than an acceleration fall threshold for at least a minimum amount of time. For example:

If $((A_w^z)^2 < \text{Th\_Accel}_{fall\ max}$ and $t_{fall} > \text{Th\_Time}_{fall\ min})$  Equation 3:

and/or

If $(|A_w^z| < \text{Th\_Accel}_{fall\ max}$ and $t_{fall} > \text{Th\_Time}_{fall\ min})$  Equation 4:

Various aspects of the disclosure may also comprise a time fall threshold beyond which a potential fall is disqualified. For example, if a fall is detected that continues for an inordinately long time, the potential fall may be deemed to be a non-fall. For example, there may be some other reason for the sensor readings different from a fall, for example a stuck accelerometer or other errant sensor state.

In an example implementation in which a maximum time fall threshold is utilized, block 310 may comprise determining whether the fall time is greater than the minimum time fall threshold and less than the maximum time fall threshold. For example, such an implementation may comprise incorporating $(\text{Th\_Time}_{fall\ min} < t_{fall} < \text{Th\_Time}_{fall\ max})$ into any of equations 2-4.

Though the discussion herein generally focuses on processing accelerometer signals to detect a fall, other sensor signals may be utilized, for example instead of or in addition to accelerometer signals. For example, a pressure sensor signal may be utilized to identify a fall. For example, block 310 may comprise monitoring and analyzing absolute pressure and/or change in pressure over time to determine whether a fall is occurring or has occurred. For example, block 310 may comprise converting the change in pressure to a device vertical position or change thereof, velocity or change thereof, and/or acceleration or change thereof. In an example implementation, a pressure sensor may be averaged and/or filtered (e.g., IIR filtered) over time to counteract noise. Also in an example implementation, for example based on an expected or determined amount of noise, a sample rate for a pressure sensor may be increased to enhance sensor resolution and/or assist with noise removal.

Block 310 may comprise storing information describing a detected fall (e.g., time and/or date information, timer/counter values, sensor data, threshold comparison results, fall duration, etc.) in a memory. Such a memory may, for example, be memory of the device (e.g., MPU internal and/or external memory). Block 310 may, for example, comprise communicating information describing a detected fall to another device (e.g., to an application processor, a networked device for example a network server, etc.). For example, block 310 may comprising storing information of a detected fall in a non-volatile memory for later reading and/or communication to a network server prior to detection of an impact (e.g., where such an impact may render the device inoperable). In such a scenario, time/date information of the fall may, for example, be stored and/or communicated for later comparison to a time/date at which a device became inoperable.

In general, block 310 may comprise performing fall detection in any of a variety of manners, non-limiting examples of which are provided herein. Accordingly, the scope of various aspects of this disclosure should not be limited by characteristics of any particular manner of performing fall detection.

After block 310, execution flow of the example method 300 may proceed to block 320. Block 320 may, for example, comprise performing impact detection (e.g., after and/or while determining that a device is falling). Block 320 may comprise performing impact detection in any of a variety of manners, non-limiting examples of which are provided herein.

By itself, a device falling might not be a concern. For example, a falling device may be softly caught, a falling device might land on a compliant surface (e.g., a cushion, a pillow, a bed, padded carpeting, etc.), a device detected as potentially falling might not have been falling at all, etc. Accordingly, detecting an impact at the end of a detected fall may be beneficial. For example, detection of an impact may help to validate a detected fall. Also for example, impact magnitude may be stored for later analysis or may be analyzed in real-time to determine whether information of the detected fall and impact is worth saving in memory or communicating to a network.

Block 320 may comprise performing impact detection by, at least in part, analyzing one or more components of an accelerometer vector expressed in body coordinates. For example, block 320 may comprise detecting if any accelerometer vector coefficient exceeds an acceleration impact threshold. For example, If $((|A_b^x| > \text{Th\_Accel}_{impact\ min})$ or
$(|A_b^y| > \text{Th\_Accel}_{impact\ min})$ or
$(|A_b^z| > \text{Th\_Accel}_{impact\ min}))$  Equation 5:

and/or

If $([|A_b^x| + |A_b^y| + |A_b^z|] \geq \text{Th\_Accel}_{impact\ min})$  Equation 6:

and/or

If $(\text{sqrt}((A_b^x)^2 + (A_b^y)^2 + (A_b^z)^2) \geq \text{Th\_Accel}_{impact\ min})$  Equation 7:

Also for example, block 320 may comprise analyzing one or more components of the accelerometer vector expressed in world coordinates. For example, block 320 may comprise determining if the z-axis coefficient of the accelerometer vector expressed in world coordinates exceeds an acceleration impact threshold. For example:

If $(|A_w^z| \geq \text{Th\_Accel}_{impact\ min})$  Equation 8:

The acceleration impact threshold $(\text{Th\_Accel}_{impact\ min})$ may, for example, be a constant that is at or near a maximum expected value for a drop impact, for example at or near the maximum output value for an accelerometer. For example, the acceleration impact threshold $(\text{Th\_Accel}_{impact\ min})$ may, for example, be at 90% of a maximum possible or expected value, 95% of a maximum possible or expected value, the maximum possible value, etc. Also for example, the acceleration impact threshold may be a maximum allowable value (e.g., over which a warrantee is void). The acceleration impact threshold $(\text{Th\_Accel}_{impact\ min})$ may, for example, be programmable. For example, in a scenario in which the MPU 120 (which may, for example, comprise a chip and/or package separate from the application processor 112 or integrated therewith) is implementing block 320, the MPU 120 may comprise an interface (e.g., a register-based interface, a FIFO-based interface, etc.) by which the application processor 112 may program any or all of the threshold values discussed herein. Note that block 320 may comprise averaging or otherwise filtering (e.g., IIR-filtering) the accelerometer vector coefficients, for example to reduce the impact of a single instantaneous signal (e.g., a noisy signal) on the calculation.

As with the fall detection discussed herein, for example with regard to block 310, block 320 may comprise performing the above calculations with squared values of one or more accelerometer vector coefficients.

The fall and impact detection performed at blocks 310 and 320 may, for example, be combined with timing information to determine a distance that a device has fallen. For example, position equations may be solved using known fall time, for example the time that passed between when a fall was first detected and when an impact is detected, and acceleration, for example assumed and/or measured. Fall distance may, for example, be utilized to determine whether a detected should be reported (e.g., storing in a memory and/or communicating to an external device).

Though the discussion herein focuses on processing accelerometer signals to detect an impact, other sensor signals may be utilized, for example instead of or in addition to accelerometer signals. For example, a pressure sensor signal may be utilized to sense an impact, identify an end of a fall from which an impact can be inferred, etc. For example, block 320 may comprise monitoring and analyzing absolute pressure and/or change in pressure over time to determine whether an impact has occurred or has likely occurred. Additionally for example, block 320 may comprise monitoring and analyzing a microphone signal to detect the impact following a fall, for example based on the sound generated by the impact.

Block 320 may comprise storing information of a detected impact (e.g., time and/or date information, timer/counter values, sensor data, threshold comparison results, impact direction and/or magnitude, etc.) in a memory. Such a memory may, for example, be memory of the device (e.g., MPU internal and/or external memory). Block 320 may, for example, comprise communicating such information to a networked device (e.g., a network server). For example, information of a detected impact may be stored in a non-volatile memory for later reading and/or communicated to a network server prior to the impact rendering the device inoperable. In such a scenario, time/date information of the impact may, for example, be stored and/or communicated for later comparison to a time/date at which a device became inoperable.

In general, block 320 may comprise performing impact detection in any of a variety of manners, non-limiting examples of which are provided herein. Accordingly, the scope of various aspects of this disclosure should not be limited by characteristics of any particular manner of performing impact detection.

After block 320, execution flow of the example method 300 may proceed to block 330. Block 330 may, for example, comprise performing no-motion (or stillness) detection (e.g., after and/or while determining that a device is falling and/or has experienced an impact). Block 330 may comprise performing no-motion detection in any of a variety of manners, non-limiting examples of which are provided herein.

By itself, a device falling and/or a device falling followed by an impact might not be indicative of a device drop event or a device drop event on a hard surface. For example, a falling device may be caught by a user with enough acceleration to be deemed to have hit the ground, a device riding in a vehicle or with a biker or on an aircraft may experience a fall followed by an impact, etc. Accordingly, detecting a state of stillness, or no-motion, at the end of a detected fall may be beneficial. For example, detection of a no-motion condition after a detected fall, and/or after a detected fall followed by an impact, may help to validate a detected fall. Also for example, information of the detected no-motion event (e.g., duration, subsequent motion information, etc.) may be stored for later analysis or may be analyzed in real-time to determine whether information of the detected fall and/or impact and/or no-motion should be stored in memory or communicated to a network.

Block 330 may comprise performing no-motion detection by, at least in part, analyzing one or more accelerometer vector coefficients, for example during a time window, to determine whether a state of no-motion exists. For example, block 330 may comprise analyzing accelerometer vector coefficients, for example during a time window, to determine whether such coefficients are all similar.

Also for example, block 330 may comprise analyzing acceleration vector and/or gyroscope vector coefficients, for example individually and/or in any combination, to determine whether they are Gaussian (or close to Gaussian). Such analysis may, for example, be performed in a time window. Non-limiting examples of such a technique are provided in U.S. patent application Ser. No. 13/164,136, titled "Motion Determination," and filed on Jun. 20, 2011, which is hereby incorporated herein by reference in its entirety. See, for example, FIGS. 1-15 and the discussion thereof, providing non-limiting examples of determining whether there is motion. For example, low order moments (e.g., first and second moments) of a sensor vector coefficient or combination thereof may be calculated directly from sensor data, and used to determine expected high order moments (e.g., third and/or fourth moments) for a Gaussian variable. The high order moments may also be calculated directly from the sensor data and then compared to the expected high order moments for a Gaussian variable. If the variable is non-Gaussian, for example due to motion of the device, then the difference between the calculated and expected value(s) will be greater than a threshold value.

Block 330 may, for example, comprise determining whether the device is in a no-motion state for at least a no-motion threshold amount of time. Such a no-motion threshold may, for example, be set high enough to have a high degree of confidence in a detected no-motion state, yet low enough such that a fast device pick-up by a user does not upset the no-motion determination.

In general, block 330 may comprise performing no-motion detection in any of a variety of manners, non-limiting examples of which are provided herein. Accordingly, the scope of various aspects of this disclosure should not be limited by characteristics of any particular manner of performing no-motion detection.

After block 330, execution flow of the example method 300 may proceed to block 340. Block 340 may, for example, comprise performing drop detection (e.g., after and/or while determining that a device is falling and/or has experienced an impact and/or has experienced a no-motion condition). Block 340 may comprise performing no-motion detection in any of a variety of manners, non-limiting examples of which are provided herein.

Block 340 may, for example, comprise determining that a qualified fall (e.g., as detected at block 310) followed by a qualified impact (e.g., as detected at block 320) followed by a qualified no-motion condition (e.g., as detected at block 330) is a device drop.

Also for example, block 340 may comprise determining that two detections out of three at blocks 310, 320, and 330 qualify as a device drop, for example so long as the one detection out of three that did not meet the criteria met at least a threshold indicative of a potential detection. For example, each of blocks 310, 320, and 330 may comprise performing detections at different respective degrees of confidence. Two relatively high-confidence detections (e.g., at two of blocks 310, 320, and 330) combined with a mid-confidence detection (e.g., at one of blocks 310, 320, and 330) may result in block 340 determining that a device has been dropped.

Block 340 may comprise storing information of a detected drop (e.g., time and/or date information, timer/counter values, sensor data, threshold comparison results, impact direction and/or magnitude, fall detection parameters, impact detection parameters, no-motion detection parameters, etc.) in a memory. Such a memory may, for example, be memory of the device (e.g., MPU internal and/or external memory). Block 340 may, for example, comprise communicating such information to a networked device (e.g., a network server). For example, information of a detected drop may be stored in a non-volatile memory for later reading and/or communicated to a network server prior to the drop rendering the device inoperable. In such a scenario, time/date information of the drop may, for example, be stored and/or communicated for later comparison to a time/date at which a device became inoperable.

In an example scenario, block 340 may comprise storing information of a detected device drop (or detected fall, detected impact, and/or detected no-motion state) in a FIFO that is generally utilized for communicating data over a bus. Block 340 may, for example, comprise constructing an information packet or frame with a header that identifies the type of information contained in the packet or frame, and place the information packet or frame in a FIFO (or other transmit buffer) for immediate transmission. The packet may, for example, comprise one or more fields for fall information, one or more fields for impact information, one or more fields for no-motion detection information, etc. The FIFO may, for example, reside on a same chip and/or in the same package as the circuitry that performs the analysis discussed herein. The FIFO may also, for example, reside on a different chip and/or in a different package, for example on a hub circuit that aggregates and communicates information for a plurality of sensor circuits.

Additionally for example, block 340 may comprise generating different interrupt signals depending on how often an event generally occurs. For example, since detected falls happen relatively less often than general sensor data communication to a host processor, a first interrupt may be generated to notify a host processor of a pending data communication and/or other events that occur regularly, and a second interrupt may be generated to notify the host processor of a pending communication associated with events that occur relatively rarely, for example device drop events, tap events, shake events, etc. For example, block 340 may comprise generating the second interrupt to notify the host processor of a detected device drop (or fall, or impact, or no-motion, etc.). In response to the second interrupt, the host processor may send a query to the sensor circuit implementing the method 300, which may then respond to such a query by communicating the information of the detected device drop to the host processor.

Further for example, block 340 (or another block, for example a configuration block) may comprise providing an interface that provides for configuring (or controlling) the manner in which block 340 (or any other block) communicates information of detected device drops, falls, impacts, and/or no-motion events to other circuits (e.g., to a host processor). For example, a host processor may determine that it wants the circuit (e.g., an MPU) implementing the method 300 to utilize the FIFO-based communication discussed herein, and the host processor may communicate configuration information to the circuit indicating to the circuit that it is to utilize such FIFO-based communication. Step 340 may then, for example, select a communication protocol to utilize to communicate the information of a detected device drop (e.g., to a host processor).

In general, block 340 may comprise performing drop detection in any of a variety of manners, non-limiting examples of which are provided herein. Accordingly, the scope of various aspects of this disclosure should not be limited by characteristics of any particular manner of performing drop detection.

After block 340, execution flow of the example method 300 may proceed to block 395. Block 395 may, for example, comprise performing any of a variety of different types of continued processing. For example, block 395 may comprise looping execution flow of the method 300 back to any previous block. Also for example, block 395 may comprise setting a timer, the expiration of which may cause the flow of the method 300 to return to any previous block. Additionally for example, block 395 may, for example after a detected drop and/or impact, comprise performing device diagnostics to determine whether the detected drop and/or impact has resulted in a component failure, degradation, etc. In such a scenario, block 395 may comprise communicating the results of the diagnostics to a network server and/or storing the results in a memory (e.g., a non-volatile memory) of the device.

In general, block 395 may comprise performing continued processing. Accordingly, the scope of various aspects of this disclosure should not be limited by characteristics of any particular type of continued processing.

As mentioned with regard to block 395, execution flow may return to any previous block in the method 300. Such flow control may exist at any or all of the method blocks discussed herein. For example, if block 320 does not detect a qualifying impact following a detected fall condition, block 320 may comprise directing execution flow of the method 300 back up to blocks 305 or 310. Also for example, if block 330 does not detect a qualifying no-motion condition following a detected fall and impact, block 330 may comprise directing execution flow of the method 300 back up to any previous block.

Various aspects of this disclosure will now be presented in view of another example flow diagram. Turning now to the discussion of FIG. 4, such figure shows a flow diagram illustrating an example method 400 for determining whether a device has been dropped, in accordance with various aspects of the present disclosure. The method 400 may, for example, share any or all characteristics with the method 300 discussed herein. Any or all of the blocks of the example method 400 may, for example, be implemented by the MPU 120 of the device 100 shown in FIG. 1, for example executing software instructions stored in the drop detection software module 142. Additionally for example, any or all of the blocks of the example method 400 may be implemented by the application (or host) processor 112 of the device 100 shown in FIG. 1, for example executing software instructions stored in the external memory 116.

Figure 4:
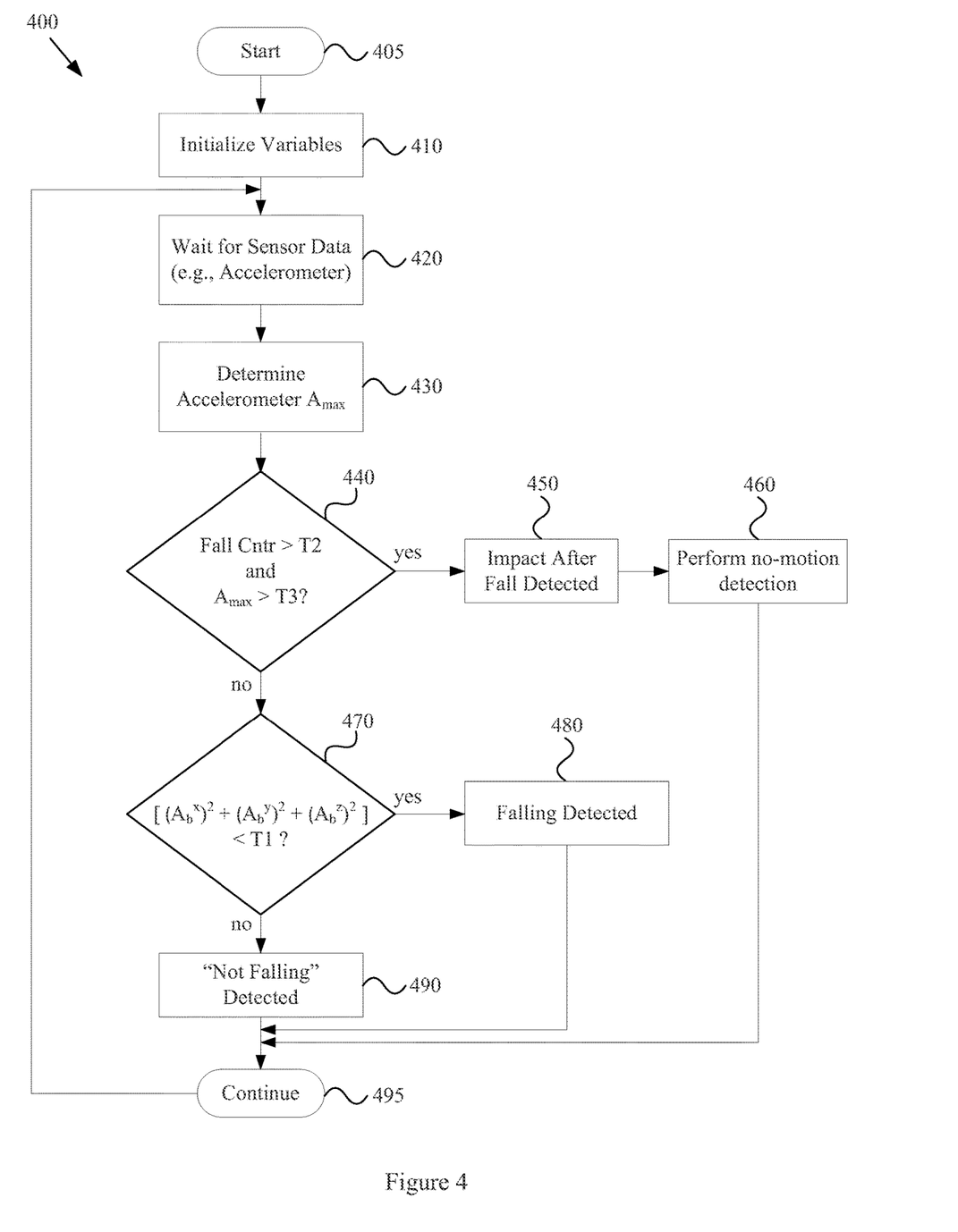
FIG. 4 shows a flow diagram illustrating an example method for determining whether a device has been dropped, in accordance with various aspects of the present disclosure.

The example method 400 may begin executing at block 405. The method 400 may begin executing in response to any of a variety of causes or conditions. For example, the method 400 may continually (e.g., periodically) run. For example, the method 400 may begin executing at a constant period (e.g., every 10 ms, every 50 ms, every 100 ms, every 200 ms, etc.). Additionally for example, the method 400 may begin operating when sensor information being analyzed is updated (e.g., at a sensor update rate). Also for example, the method 400 may begin executing in response to a substantial noise (e.g., an audible exclamation that often accompanies a dropped device, the sound of a phone being removed from a pocket or purse, etc.). Further for example, the method 400 may begin executing in response to one or more sensors (or a sensor fusion output) indicating that the orientation and/or elevation of the device has substantially changed (e.g., based on a rotation that often accompanies a falling device). In general, the method 400 may begin executing in response to any of a variety of causes or conditions. Accordingly, the scope of various aspects of this disclosure should not be limited by characteristics of any particular one or more causes or conditions.

From block 405, execution flow of the example method 400 proceeds to block 410. Block 410 may, for example, comprise initializing any of a variety of variables or parameters. Such variables or parameters may, for example, comprise timer or counter parameters, comparison thresholds, accumulators, etc. Note that in various example scenarios, block 410 may comprise retrieving values (e.g., threshold values) from registers or memory locations programmed by the application (or host) processor. For example, referring to FIG. 1, block 410 may comprise the sensor processor 130 retrieving from and/or setting parameters in the internal memory 140. Some or all of such parameters may, for example, have been previously received from the application processor 112 (e.g., at system initialization, in response to real-time operating conditions, in response to an adaptive operation algorithm, etc.).

After block 410, execution flow of the example method 400 proceeds to block 420. Block 420 may, for example, comprise waiting to receive sensor data (e.g., raw sensor data and/or motion data) to process. Such waiting may, for example, be passive (e.g., passively listening on a channel over which sensor information is communicated) or active (e.g., including communicating a request for the desired sensor information to a source of such information followed by listening for a response to the request. In an example scenario, block 420 comprises waiting for accelerometer data (e.g., raw data or motion data) indicative of acceleration forces experienced by the device 100 and/or MPU 120. Referring briefly to FIG. 1, the sensor processor 130 (e.g., operating pursuant to software instructions in the drop detection module 142) may wait to receive sensor data information directly from the internal sensor(s) 150 and/or the external sensor(s) 116. Additionally for example, the sensor processor 130 (e.g., operating pursuant to software instructions in the drop detection module 142) may wait to receive sensor data information after being processed by other modules (e.g., by the sensor fusion module 144).

After block 410, execution flow of the example method 400 proceeds to blocks 430 and 440. Blocks 430 and 440 may, for example, comprise performing impact detection. Blocks 430 and 440 may, for example, share any or all characteristics with block 320 of the method 300 shown in FIG. 3 and discussed herein. In the particular example illustrated, blocks 430 and 440 comprise determining whether a maximum acceleration value from an accelerometer exceeds an acceleration impact threshold. Block 440 may also comprise determining whether a detected fall prior to the detected impact was long enough, for example by comparing a fall counter to a threshold value. Block 440 may thus, for example, also share any or all characteristics with block 310 of the method 300 shown in FIG. 3 and discussed herein.

Block 440 may, for example if the acceleration is high enough to be deemed a valid impact for a device drop and the fall time is great enough to be deemed a valid fall for a device drop, direct execution flow of the example method 400 to block 450, indicating that a qualifying impact after a qualifying fall has been detected. After block 450, execution of the example method 400 flows to block 460 for performing no-motion detection. Block 460 may, for example, share any or all characteristics with block 330 of the example method 300 illustrated in FIG. 3 and discussed herein.

If block 440 determines that a qualifying impact has not occurred after a qualifying fall, then block 440 may comprise directing execution flow of the example method 400 to block 470, which comprises determining if the device is falling. Block 470 may, for example, share any or all characteristics with block 310 of the example method 300 illustrated in FIG. 3 and discussed herein. Block 470 may, for example, comprise performing at least a portion of Equation 1 to ascertain whether the device is in a falling state. If block 470 determines that the device is in a falling state, then block 470 may comprise directing execution flow of the method 400 to block 480, which may for example comprise incrementing a falling counter. If block 470 determines that the device is not in a falling state, then block 470 may comprise directing execution flow of the method 400 to block 490, which may for example comprise resetting the falling counter.

After any of blocks 460, 480, and/or 490, execution of the method 400 may flow to block 495 for continued processing. Block 495 may, for example, share any or all characteristics with block 395 of the example method 300 illustrated in FIG. 3 and discussed herein. For example, block 495 may comprise directing execution flow of the method 400 to any previous block, for example immediately or after execution of a timer.

Figure 5:
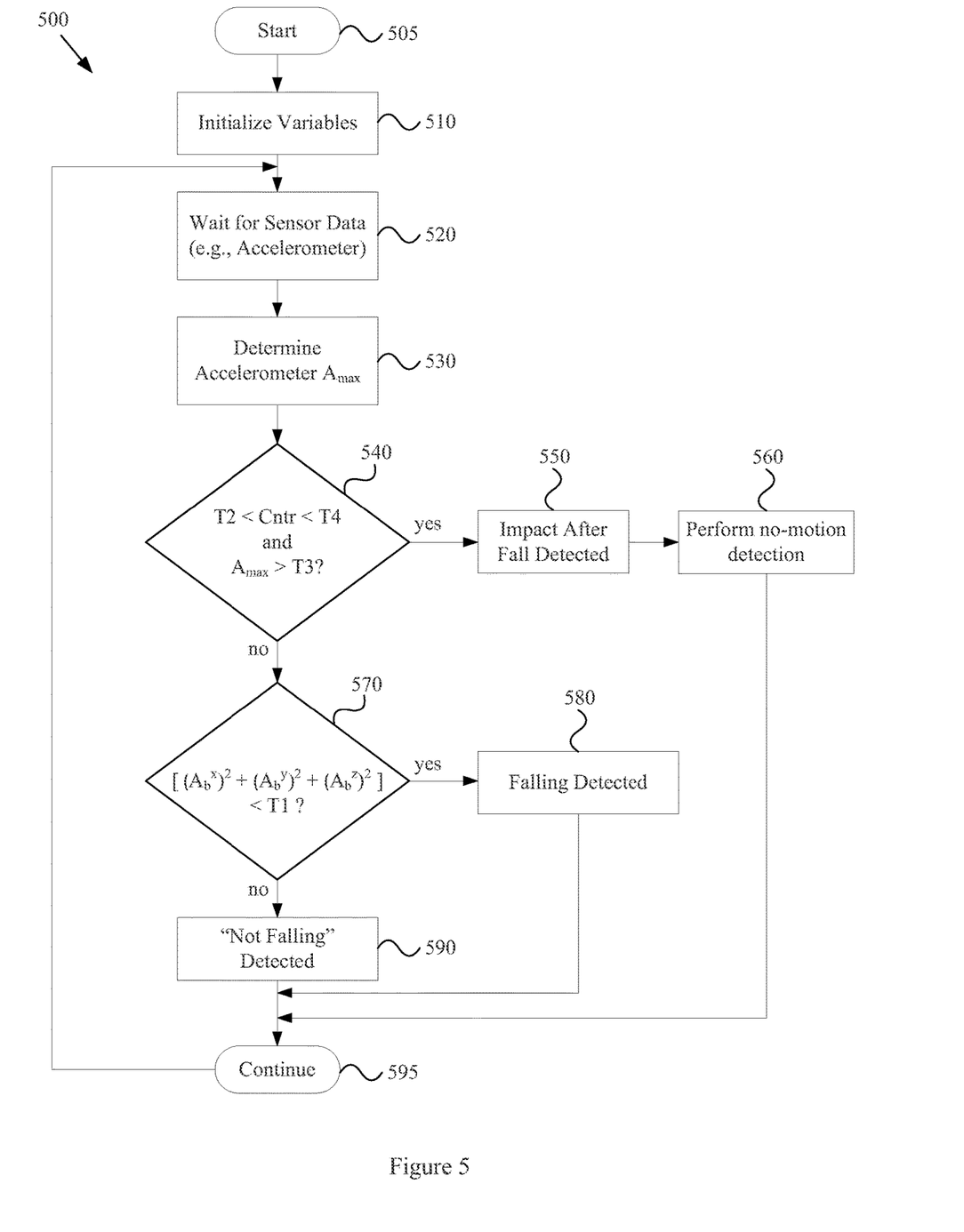
FIG. 5 shows a flow diagram illustrating an example method for determining whether a device has been dropped, in accordance with various aspects of the present disclosure.

Turning next to FIG. 5, such figure shows a flow diagram illustrating an example method 500 for determining whether a device has been dropped, in accordance with various aspects of the present disclosure. The method 500 may, for example, share any or all characteristics with the methods 400 and/or 300 discussed herein. Any or all of the blocks of the example method 500 may, for example, be implemented by the MPU 120 of the device 100 shown in FIG. 1, for example executing software instructions stored in the drop detection software module 142. Additionally for example, any or all of the blocks of the example method 500 may be implemented by the application (or host) processor 112 of the device 100 shown in FIG. 1, for example executing software instructions stored in the external memory 116.

The primary difference between example method 500 and example method 400 is at block 540. Thus, only block 540 will be discussed at this point. As mentioned previously in the discussion of block 310, a fall that is detected for too long of a time may be an indication of a stuck sensor or other problem. Accordingly, various aspects of this disclosure may comprise incorporating (Th_Time$_{fall\ min}$<t$_{fall}$<Th_Time$_{fall\ max}$) into, for example any of equations 2-4 and the like. Such a dual-threshold comparison is indicated at block 540. For example, for block 540 to determine that a qualified impact-after-fall has occurred, the fall counter has to be greater than a minimum fall time threshold and also less than a maximum fall time threshold.

As discussed herein, any one or more of the modules and/or functions discussed herein may be implemented by a processor (e.g., an application or host processor, a sensor processor, etc.) executing software instructions. Similarly, other embodiments may comprise or provide a non-transitory computer readable medium and/or storage medium, and/or a non-transitory machine readable medium and/or storage medium, having stored thereon, a machine code and/or a computer program having at least one code section executable by a machine and/or a computer (or processor), thereby causing the machine and/or computer to perform the methods as described herein.

In summary, various aspects of the present disclosure provide a system and method for detecting when a device has been dropped. While the foregoing has been described with reference to certain aspects and embodiments, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular embodiment(s) disclosed, but that the disclosure will include all embodiments falling within the scope of the appended claims.

What is claimed is:

1. A system for drop detection, the system comprising: a mobile device having a motion sensor; at least one module that is operable to, at least: perform fall detection; perform impact detection; perform no-motion detection; and perform device drop detection, based at least in part on the fall detection, the impact detection, and the no-motion detection, wherein the fall detection, impact detection and the no-motion detection are based at least in part on data from the motion sensor, wherein performing no-motion detection occurs after at least one of the fall detection and impact detection and wherein the at least one module is operable to perform no-motion detection by, at least in part, analyzing moments of a sensor signal to determine whether the sensor signal is close to Gaussian.

2. The system of claim 1, wherein the motion sensor comprises an accelerometer and wherein the at least one module is operable to perform fall detection by, at least in part, determining whether one or more accelerometer signals are of negligible amplitude.

3. The system of claim 2, wherein the at least one module is operable to perform fall detection by, at least in part, determining whether one or more accelerometer signals are of negligible amplitude for at least a minimum threshold amount of time.

4. The system of claim 3, wherein the at least one module is operable to perform fall detection by, at least in part, determining whether one or more accelerometer signals are of negligible amplitude for at least a minimum threshold amount of time and for no more than a maximum threshold amount of time.

5. The system of claim 2, wherein the at least one module is operable to perform fall detection by, at least in part, analyzing a plurality of accelerometer signals in a body coordinate system.

6. The system of claim 2, wherein the at least one module is operable to perform fall detection by, at least in part, analyzing a z-axis accelerometer signal in a world coordinate system.

7. The system of claim 1, wherein the motion sensor comprises an accelerometer and wherein the at least one module is operable to perform impact detection by, at least in part, determining whether an accelerometer signal is at least a minimum threshold.

8. The system of claim 7, wherein the at least one module is operable to perform impact detection by, at least in part, analyzing a plurality of accelerometer signals in a body coordinate system.

9. The system of claim 7, wherein the at least one module is operable to perform impact detection by, at least in part, analyzing a z-axis accelerometer signal in a world coordinate system.

10. The system of claim 1, wherein the at least one module is operable to perform no-motion detection by, at least in part, detecting no motion for at least a minimum threshold amount of time.

11. The system of claim 1, wherein said analyzing moments of a sensor signal comprises: calculating first and second moments of a sensor signal directly from sensor data; determining a determined higher order moment based, at least in part, on the calculated first and second moments; calculating a calculated higher order moment of the sensor signal directly from sensor data; calculating a difference between the determined higher order moment and the calculated higher order moment; and determining whether the sensor signal is close to Gaussian by, at least in part, comparing the calculated difference to a threshold value.

12. The system of claim 1, wherein the at least one module is operable to turn off a display upon detection of an impact and/or detection of a drop.

13. The system of claim 1, wherein the at least one module is contained in a single integrated circuit package.

14. A sensor circuit for performing drop detection, the sensor circuit comprising: a motion sensor; at least one module that is operable to, at least: perform fall detection; perform impact detection; perform no-motion detection; perform device drop detection, based at least in part on the fall detection, the impact detection, and the no-motion detection, and communicate information of a detected device drop to a host processor, wherein the fall detection, impact detection and the no-motion detection are based at least in part on data from the motion sensor, wherein performing no-motion detection occurs after at least one of the fall detection and impact detection and wherein the at least one module is operable to perform no-motion detection by, at least in part, analyzing moments of a sensor signal to determine whether the sensor signal is close to Gaussian.

15. The sensor circuit of claim 14, wherein the at least one module is operable to communicate information of a detected device drop to a host processor by, at least in part: communicating an interrupt signal to the host processor; receiving a query from the host processor; and in response to the received query, communicate the information of the detected device drop to the host processor.

16. The sensor circuit of claim 15, wherein the interrupt signal is a different type of interrupt signal than used by the sensor circuit for communicating general sensor information to the host processor.

17. The sensor circuit of claim 14, wherein the at least one module is operable to communicate the information of a detected device drop to a host processor by, at least in part, loading the information of a detected device drop into a transmit buffer for transmission to the host processor.

18. The sensor circuit of claim 17, wherein the at least one module is operable to communicate the information of a detected device drop to a host processor by, at least in part, loading the information of a detected device drop into a data structure comprising: a header identifying the data structure as a data structure that communicates information of detected device drops; and one or more data fields describing characteristics of the detected device drop.

19. The sensor circuit of claim 14, wherein the at least one module is operable to communicate the information of a detected device drop to the host processor by, at least in part, selecting one of a plurality of communication protocols for communicating information of a detected device drop.

20. The sensor circuit of claim 19, wherein the selecting one of a plurality of communication protocols comprises selecting the one of the plurality of communication protocols based, at least in part, on configuration information for the sensor circuit received from the host processor.

21. The sensor circuit of claim 14, wherein the at least one module is contained in a single integrated circuit package.

22. A sensor circuit for performing drop detection, the sensor circuit comprising: a motion sensor; at least one module that is operable to, at least: perform fall detection; perform impact detection; perform no-motion detection; perform device drop detection, based at least in part on the fall detection, the impact detection, and the no-motion detection; and provide an interface by which a host processor may program a threshold value used by the at least one module in performing the fall detection, the impact detection, the no-motion detection, and/or the device drop detection, wherein the fall detection, impact detection and the no-motion detection are based at least in part on data from the motion sensor, wherein performing no-motion detection occurs after at least one of the fall detection and impact detection and wherein the at least one module is operable to perform no-motion detection by, at least in part, analyzing moments of a sensor signal to determine whether the sensor signal is close to Gaussian.

23. The sensor circuit of claim 22, wherein the motion sensor comprises an accelerometer and wherein the at least one module is operable to perform fall detection by, at least in part, utilizing the programmed threshold value to determine whether one or more accelerometer signals are of negligible amplitude.

24. The sensor circuit of claim 22, wherein the at least one module is operable to perform fall detection by, at least in part, utilizing the programmed threshold value to determine whether one or more accelerometer signals are of negligible amplitude for at least the programmed threshold amount of time.

25. The sensor circuit of claim 22, wherein the at least one module is operable to perform impact detection by, at least in part, utilizing the programmed threshold value to determine whether an accelerometer signal is at least a minimum threshold.

26. The sensor circuit of claim 22, wherein the at least one module is operable to perform no-motion detection by, at least in part, utilizing the programmed threshold value to detect no motion for at least the programmed threshold amount of time.

27. The system of claim 1, wherein said analyzing moments of a sensor signal comprises:
   determining an average of data values; wherein the sensor signal comprises the data values as a function of user motion and noise and the average of the data values comprises a first order moment;
   determining an average of squares of the data values; wherein the average of the squares of the data values comprises a second order moment;
   determining an average of cubes of the data values; and
   determining a difference between a third order moment calculated only using the average of cubes and a third order moment calculated using only the first and second order moments,
   wherein the at least one module is operable to perform the no-motion detection based on the difference.

28. The system of claim 27, wherein said analyzing moments of a sensor signal further comprises:
   determining an average of fourth powers of the data values; and
   determining a second difference between the average of the fourth powers and an expected fourth order moment, wherein the expected fourth order moment is calculated from the average of the squares and the average of the data values,
   wherein the at least one module is operable to perform the no-motion detection based on the second difference.

29. The system of claim 27, wherein said analyzing moments of a sensor signal further comprises:
   determining an average of fourth powers of the data values;
   determining an average of fifth powers of the data values;
   determining a third difference between the average of the fifth powers and an expected fifth order moment, wherein the expected fifth order moment is calculated from the average of the squares and the average of the data values; and
   wherein the at least one module is operable to perform the no-motion detection based on the third difference.

* * * * *